(12) United States Patent
Shimada et al.

(10) Patent No.: US 6,454,747 B1
(45) Date of Patent: Sep. 24, 2002

(54) DISPOSABLE DIAPER

(75) Inventors: Takaaki Shimada; Seiji Suzuki, both of Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 09/472,253

(22) Filed: Dec. 27, 1999

(30) Foreign Application Priority Data

Dec. 28, 1998 (JP) .......................................... 10-374169

(51) Int. Cl.⁷ .................................................. A61F 7/00
(52) U.S. Cl. ........................ 604/312; 604/604; 604/378; 604/385.01; 604/385.3; 604/396
(58) Field of Search ................... 604/385.29–285.31, 604/393–394, 396, 385.01, 378, 312

(56) References Cited

U.S. PATENT DOCUMENTS

| | | | |
|---|---|---|---|
| 3,929,135 A | * | 12/1975 | Thompson |
| 4,573,986 A | * | 3/1986 | Minetola et al. |
| 4,775,579 A | * | 10/1988 | Hagy et al. |
| 5,019,066 A | | 5/1991 | Freeland et al. |
| 5,074,854 A | * | 12/1991 | Davis |
| 5,114,420 A | * | 5/1992 | Igaue et al. ............ 604/385.26 |
| 5,531,729 A | * | 7/1996 | Coles et al. |
| 5,718,698 A | | 2/1998 | Dobrin et al. |

FOREIGN PATENT DOCUMENTS

| | | |
|---|---|---|
| EP | 0 403 832 | 12/1990 |
| JP | 5-41525 | 6/1993 |

* cited by examiner

Primary Examiner—John G. Weiss
Assistant Examiner—K. M. Reichle
(74) Attorney, Agent, or Firm—Baker & Daniels

(57) ABSTRACT

A disposable diaper that includes an absorbent unit and a breathable sweat-absorbent sheet. An end flap is formed in a rear waist region of the absorbent unit and is arranged to be breathable. The sweat-absorbent sheet is bonded to the inner surface of the end flap. The diaper thus constructed is breathable and sweat absorbable in the waist region of the absorbent unit.

7 Claims, 3 Drawing Sheets

DISPOSABLE DIAPER

BACKGROUND OF THE INVENTION

This invention relates to a disposable diaper adapted to absorb and contain body wastes.

Such a diaper is usually provided along the end flaps defining the waist band region with elastic members so that contraction of these elastic members may function to press the diaper against a wearer's skin and thereby prevent the diaper from getting out of shape or from slipping down during use. Consequently, perspiration occurs along the region of the wearer's skin against which the end flaps are pressed. Such oppression and perspiration give the wearer an unpleasant feeling and may cause various skin diseases such as eczema, eruption and heat rash.

To overcome this adverse affection of perspiration, it is well known, for example, from Japanese Utility Model Application Disclosure Gazette (Kokai) No. Hei5-41535 to detachably attach a sweat-absorbent sheet of cotton cloth to the inner surface of the rear waist region.

The Japanese Utility Model Application Disclosure Gazette (Kokai) No. Hei5-41525 discloses providing the rear waist band region with a sweat-absorbent sheet of cotton cloth. However, it is difficult for such a diaper to avoid the unpleasant feeling and skin diseases merely by providing a sweat-absorbent sheet, because it has been found that the waist band region of the diaper should be sweat-absorbent and, at the same time, sufficiently breathable to avoid such problems.

SUMMARY OF THE INVENTION

It is an object of this invention to compose at least one of the end flaps in the front and rear waist regions defining the waist band region in such a manner that the end flap may have not only a ventilating function but also a sweat-absorbing function.

According to this invention, there is provided a disposable diaper having a front waist region, a rear waist region and a crotch region, the diaper comprising an absorbent unit including a liquid-pervious topsheet, a liquid-impervious backsheet and a liquid-absorbent core disposed between the topsheet and the backsheet, said backsheet including a breathable outer layer and a liquid-impervious inner layer laminated with an inner surface of said breathable outer layer, and, in said front and rear waist regions, a pair of end flaps extending outward beyond longitudinally opposite ends of said absorbent core.

In such a disposable diaper, at least one of the end flaps in said front and rear waist regions includes a region having a predetermined dimension defined between a longitudinal end of the end flap and the longitudinal end of the absorbent core adjacent to the longitudinal end of the end flap, the region having the predetermined dimension is formed by portions of the breathable outer layer and the liquid-pervious topsheet that extend outward beyond the longitudinal end of the absorbent core and further being provided on an inner surface thereof with a breathable sweat-absorbent sheet bonded thereto so as to cover the region having the predetermined dimension.

This invention includes alternative embodiments wherein the breathable sweat-absorbent sheet contains at least 20% by weight of hydrophilic fibers; wherein the breathable sweat-absorbent sheet comprises a laminate having an upper layer containing at least 20% by weight of hydrophilic fibers and is intended to. come in contact with a wearer's skin and a lower layer formed from hydrophobic fibers which is intended not to come in contact with the wearer's skin; wherein the breathable sweat-absorbent sheet has a plurality of pores each having a diameter of 0.1~3 mm; wherein the breathable sweat-absorbent sheet is bonded to the end flap intermittently at least in a circumferential direction of the diaper; the end flap having the breathable sweat-absorbent sheet bonded thereto is provided with elastic members adapted to be stretchable and contractable in the circumferential direction of the diaper; and the outer layer of the backsheet is formed from a nonwoven fabric and the inner layer of the backsheet is formed from a plastic film.

DETAILED DESCRIPTION ON THE PREFERRED EMBODIMENTS

Details of this invention will be more fully understood from the description of a disposable pull-on diaper which is provided as a specific embodiment of the invention given hereunder with reference to the accompanying drawings.

Figure 1:
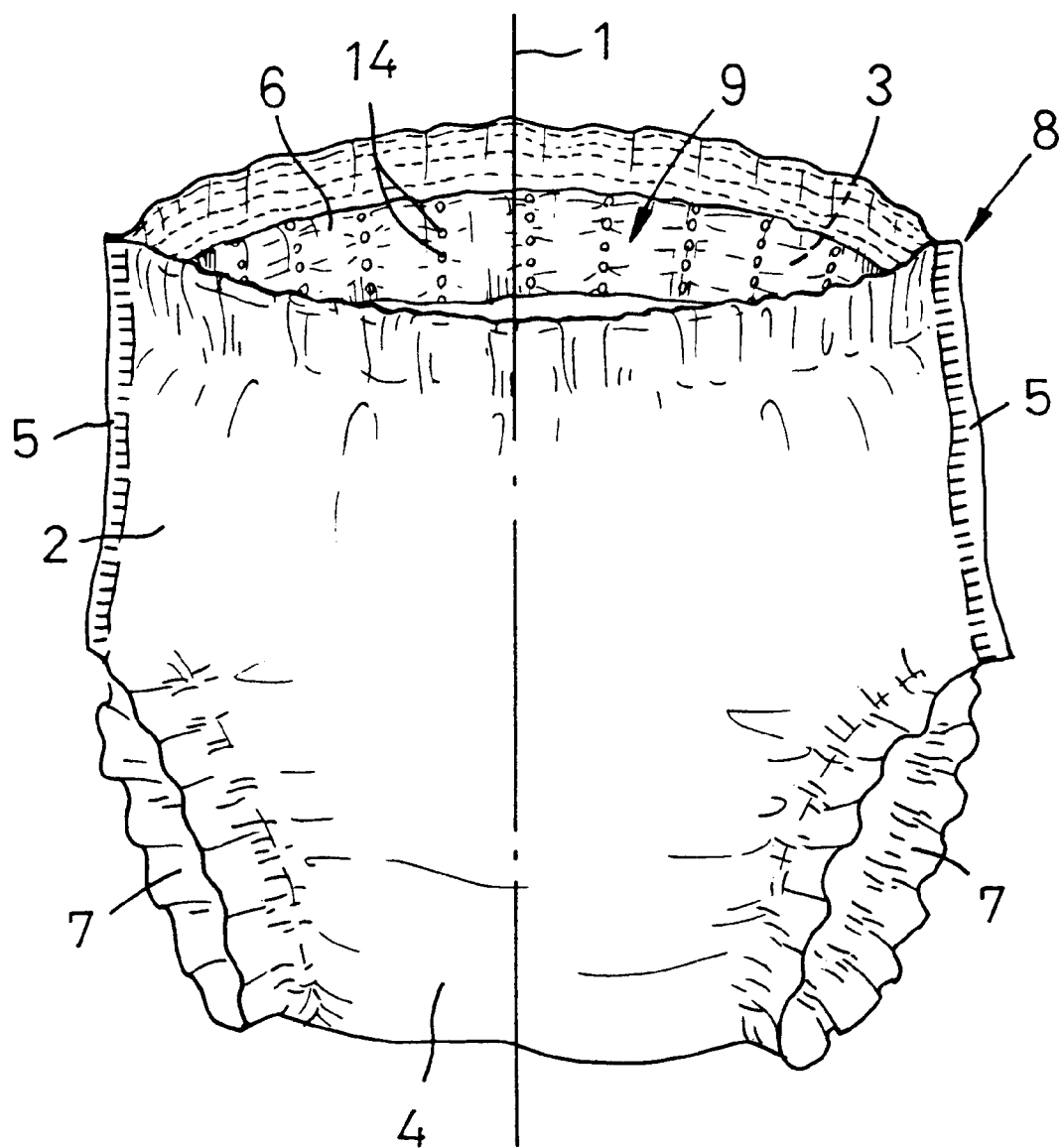
FIG. 1 is a perspective view of a pull-on disposable diaper which is presented as a specific embodiment of this invention.

Referring to FIG. 1, a diaper is bilaterally configured about a center line 1 extending in its longitudinal direction and has a front waist region 2, a rear waist region 3 and a crotch region 4. The front and rear waist regions 2, 3 are bonded to each other intermittently along their transversely opposite side edges 5, 5 to define an elastic waist-opening 6 and a pair of elastic leg-openings 7, 7.

Figure 2:
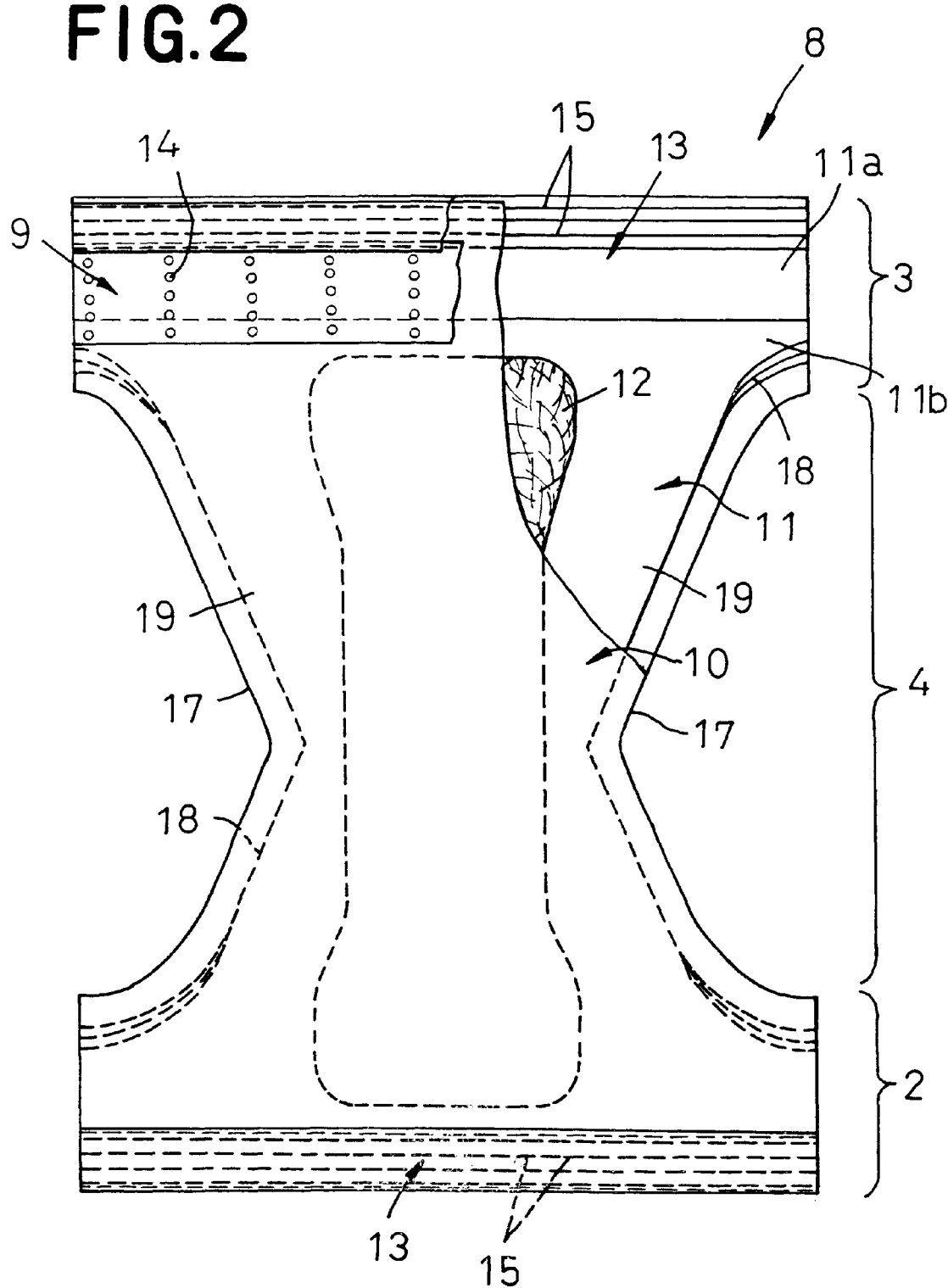
FIG. 2 is a plan view showing the partially cutaway and developed diaper.
Figure 3:
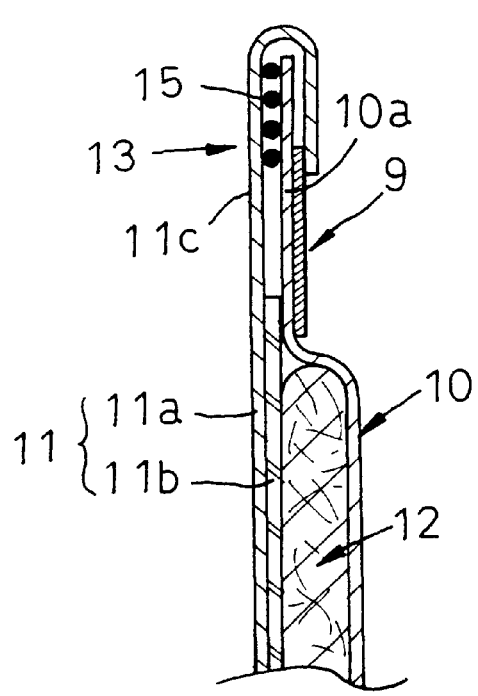
FIG. 3 is a sectional view showing, in an enlarged scale, a rear waist region and its vicinity.

Referring to FIGS. 2 and 3, the diaper comprises of an absorbent unit 8 and a breathable sweat-absorbent sheet 9. The absorbent unit 8 comprises a liquid-pervious topsheet 10, a liquid-impervious backsheet 11 and a liquid-absorbent core 12 disposed between these two sheets 10, 11. The backsheet 11 comprises, in turn, a breathable outer layer 11a and a liquid-impervious inner layer 11b integrally laminated on the inner surface of the breathable outer layer 11a by suitable means (not shown) such as well known sealing techniques or use of adhesives. The topsheet 10 and the backsheet 11 extend outward beyond a peripheral edge of the absorbent core 12 and the extensions of the sheets 10, 11 cooperate with each other to form longitudinally opposite end flaps 13 that define waist-band regions for the front and rear waist regions, respectively, and transversely opposite side flaps 19 (See FIG. 1). It should be understood that the end flaps 13 substantially comprise the outer layer 11a of the backsheet 11 and the topsheet 10, because the portion of the inner layer 11b of the backsheet 11 which extends beyond the peripheral edge of the absorbent core 12 is extremely small. The breathable sweat-absorbent sheet 9 extends circumferentially of the diaper along the end flap 13 in the rear waist region. The sweat-absorbent sheet 9 is bonded to the upper surface of the topsheet 10 utilizing the well known bonding means 14 such as hot melt adhesive, heat-emboss/deboss or heat-sealing intermittently in the circumferential direction as well as in the longitudinal direction of the diaper. The outer layer 11a of the backsheet 11 which forms one component of the end flap 13 has a longitudinal dimension larger than that of the topsheet 10 and is folded back onto and bonded to the topsheet 10 by the means (not shown) similar to those as have been described above. A plurality of elastic members 15 adapted to be stretchable and contractible circumferentially of the diaper are provided between an extension 11c of the outer later 11a and an extension 10a of the topsheet 10 which together form the end flap 13. The plurality of elastic members are bonded to the extensions 11c, 10a by hot melt adhesive of well known art (not shown).

Figure 4:
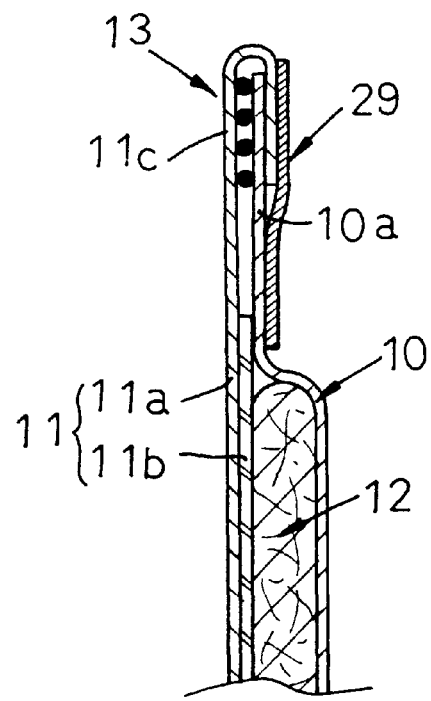
FIG. 4 is a view similar to FIG. 3 showing a rear waist region and its vicinity according to an embodiment differing from the embodiment shown in FIG. 3.

The embodiment shown in FIG. 4 is similar to the embodiment shown in FIG. 3 except that a breathable sweat-absorbent sheet 29 is wider than the breathable sweat-absorbent sheet 9 and bonded to substantially the entire inner surface of the end flap 13 including a portion of the extension 11c of the outer layer 11a making a part of the backsheet 11 which has been folded back onto the topsheet 10.

Without departing from the scope of this invention, the embodiments shown in FIGS. 3 and 4 may be modified so that not only the inner layer 11b of the backsheet 11, but also the topsheet 10 extend slightly into the region defined by the end flap 13 and the breathable sweat-absorbent sheet 9, 29 is directly bonded to the extension 11c of the outer sheet 11a making a part of the backsheet 11 extend substantially over the entire region of the sheet 9, 29.

Figure 5:
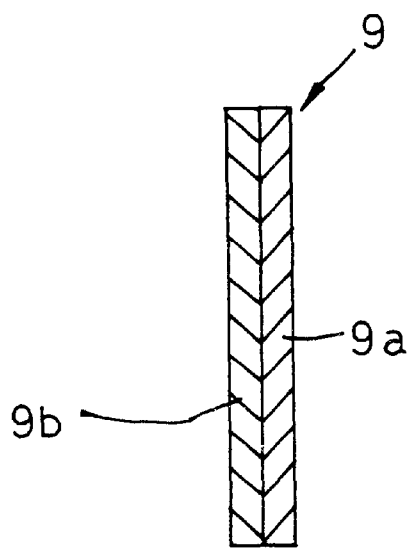
FIG. 5 is a sectional view showing an embodiment of a breathable sweat-absorbent sheet.
Figure 6:
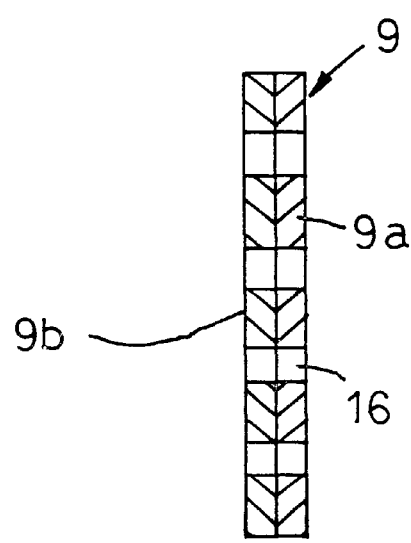
FIG. 6 is a view similar to FIG. 5 showing another embodiment of the breathable sweat-absorbent sheet.

Referring to FIGS. 5 and 6, the breathable sweat-absorbent sheet 9 preferably comprises an upper layer 9a containing at least 20% by weight of hydrophilic fibers and a lower layer 9b of hydrophobic fibers laminated integrally with the upper layer 9a taking account of desired breathability, sweat-absorbability and cushioning property. Alternatively, the breathable sweat-absorbent sheet 9, 29 may be formed from a single layer containing at least 20% by weight hydrophilic fibers. The hydrophilic fibers useful for this purpose include cellulose fibers such as rayon and sweat-absorbent polyester fibers, or the like, having fiber surfaces subjected to any hydrophiling treatment. The hydrophobic fibers useful for this purpose include polypropylene, polyester, and crimped or non-crimped polyethylene/polyester conjugated fibers. The breathable sweat-absorbent sheet 9, 29 may be provided in optional forms, for example, in the form of a spun lace, needle punched, thermal bond, spun bond, melt blown or chemical bond nonwoven fabric having a basis weight of 10~100 g/m$^2$ and a fineness of 0.1~10 d. The breathable sweat-absorbent sheet 9, 29 is preferably formed with a plurality of pores having diameters of 0.1~3 mm in order to improve breathability of the breathable sweat-absorbent sheet 9, 29.

While FIG. 2 shows the breathable sweat-absorbent sheet 9 as being provided only in the rear waist region 3 of the diaper. Taking into account that sweating occurs more significantly in a rear waist region than in a front waist region by a wearer, it is possible to provide the front waist region with a similar breathable sweat-absorbent sheet 9, if desired. This is also true for the breathable sweat-absorbent sheet 29.

Referring again to FIG. 2, the topsheet 10 and the backsheet 11 in the crotch region 4 are formed along transversely opposite side edges with cutouts 17, 17 which define the pair of leg-openings 7, 7 as shown in FIG. 1. Elastic members 18, 18 are provided along the cutouts 17, 17, and bonded by means of well known hot melt (not shown) between the topsheet 10 and the backsheet 11 so that these elastic members 18, 18 extend and are stretchable/contractable circumferentially around the respective leg-openings 7, 7. The absorbent core 12 is semi-rigid and substantially fixed by means of well known hot melt adhesive between the topsheet 10 and the backsheet 11 in order to ensure that the absorbent core 12 is protected from getting out of its initial shape. The topsheet 10 and the backsheet 11 have a high flexibility and therefore, the end flaps 13 as well as the side flaps 19 also have a relatively high flexibility. Accordingly, soft and good fitness of the diaper can be ensured around the wearer's torso and legs. While both the outer layer 11a and the inner layer 11b of the backsheet 11 are shown as extending beyond the side edges of the absorbent core 12 into the respective side flaps 19, 19 by the same dimension (See FIG. 3), an alternative arrangement is possible, in which the side edges of the inner layer 11b lie inside the side edges of the outer layer 11a. The inner layer 11b is preferably liquid-impervious and moisture-pervious so that, in addition to the breathability offered by the end flaps 13, any moisture that accumulates within the diaper can be exhausted to the exterior of the diaper to avoid undesirable stiffness.

The topsheet 10 is made from breathable nonwoven fibers, a porous plastic film or the like, the outer layer 11a of the backsheet 11 is made from a breathable nonwoven fabric or the like, the inner layer 11b of the backsheet 11 is made from a plastic film or the like, and the absorbent core 12 is made from a mixture of fluff pulp and superabsorbent polymer particles covered with an absorbent/diffusive sheet or the like. These stock materials are those usually used for disposable diapers or sanitary napkins. While the breathable sweat-absorbent sheet 9, 29 formed by any one of the above-mentioned materials effectively functions, the breathable sweat-absorbent sheet 9, 29 is preferably formed from an upper layer 9a and a lower layer 9b. The upper layer 9a is formed from a mixture of rayon fibers of 50% by weight and polypropylene fibers of 50% by weight and the lower layer 9b is formed from a mixture of polypropylene fiber of 80% by weight and core-sheath-type polyethylene/polyester conjugated fiber of 20% by weight. The breathable sweat-absorbent sheet 9, 29 may contain crimped fibers to improve its cushioning property and breathability.

The absorbent unit 8 may be also in the form of a so-called open type unit.

By wearing the diaper according to this invention as has been described heretofore, sweat spreading around the wearer's torso is effectively absorbed by the breathable sweat-absorbent sheet 9, 29 and vapor generated from evaporation of sweat is ventilated out through the outer layer 11a of the backsheet 11 in the regions of the end flaps 13, 13 where the inner layer 11b of the backsheet 11 is absent.

The unique arrangement in which the breathable sweat-absorbent sheet 9, 29 is intermittently bonded to the end flap 13 cooperates with elastic contraction of the elastic members 15 to produce many spaces between the breathable sweat-absorbent sheet 9, 29 and the extension 11c of the outer layer 11a. As a result, the ventilation through the end flap 13 is further improved and the breathable sweat-absorbent sheet 9, 29 is always maintained in a relatively high dryness.

As will be apparent from the foregoing description, in the diaper according to this invention the end flaps defining the waist band region offer a high breathability and at the same time effectively absorb the wearer's sweat so that the wearer can be protected not only from discomfort due to a stuffiness within the diaper but also against being affected with various skin diseases as have previously been described. These features enable the diaper of this invention to be advantageously used in practice.

What is claimed is:

1. A disposable diaper having a front waist region, a rear waist region and a crotch region, the diaper further comprising:

a liquid-pervious topsheet;

a liquid-impervious backsheet;

a liquid-absorbent core disposed between said topsheet and said backsheet, said backsheet including a breathable outer layer and a liquid-impervious inner layer laminated to an inner surface of said breathable outer layer; and a pair of end flaps extending outward beyond longitudinally opposite ends of said absorbent core in said front and rear waist regions, at least one of said pair of end flaps in said front and rear waist regions includes a region defined between a longitudinal end of said at least one end flap and a longitudinal end of said absorbent core adjacent to said longitudinal end of said at least one end flap, said region being formed by a portion of said breathable outer layer that extends outward beyond a longitudinal end of said liquid-impervious inner layer and a portion of said liquid-pervious topsheet that extends outward beyond said longitudinal end of said absorbent core and further being provided on an inner surface of said liquid-pervious topsheet with a breathable sweat-absorbent sheet bonded thereto so as to cover said region.

2. A disposable diaper according to claim 1, wherein said breathable sweat-absorbent sheet comprises a laminate of an upper layer containing at least 20% by weight of hydrophilic fibers and positioned to come into contact with a wearer's skin and a lower layer formed from hydrophobic fibers and positioned so as not to come into contact with the wearer's skin.

3. A disposable diaper according to claim 1, wherein said breathable sweat-absorbent sheet contains at least 20% by weight of hydrophilic fibers.

4. A disposable diaper according to claim 1, wherein said breathable sweat-absorbent sheet has a plurality of pores each having a diameter of 0.1~3 mm.

5. A disposable diaper according to claim 1, wherein said breathable sweat-absorbent sheet is bonded to said at least one end flap intermittently at least in a circumferential direction of said diaper.

6. A disposable diaper according to claim 1, wherein said at least one of said end flaps having said breathable sweat-absorbent sheet bonded thereto is provided with elastic members that are stretchable and contractible in a circumferential direction of said diaper.

7. A disposable diaper according to claim 1, wherein said outer layer of said backsheet is formed from a nonwoven fabric and said inner layer of said backsheet is formed from a plastic film.

* * * * *